US006441176B1

(12) United States Patent
Tom

(10) Patent No.: US 6,441,176 B1
(45) Date of Patent: Aug. 27, 2002

(54) METHOD FOR PREPARING SODIUM-HYDROGEN EXCHANGER TYPE 1 INHIBITOR

(75) Inventor: Norma J. Tom, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/636,406

(22) Filed: Aug. 10, 2000

Related U.S. Application Data

(60) Provisional application No. 60/162,377, filed on Oct. 29, 1999.

(51) Int. Cl.[7] ...................... C07D 401/04; C07D 215/38
(52) U.S. Cl. ...................... 546/167; 546/171; 560/124; 564/230
(58) Field of Search ................................ 546/167, 171; 560/124; 564/230

(56) References Cited

U.S. PATENT DOCUMENTS 4,028,381 A * 6/1977 Gschwend .............. 260/310 R
6,184,380 B1 * 2/2001 Chiu ......................... 546/123

FOREIGN PATENT DOCUMENTS

WO 9943663 9/1999
WO WO 0130759 5/2001

OTHER PUBLICATIONS

Manfred Baumgarth, et al, J. Med. Chem. 1997, 40, 2017–2034, "(2–Methyl–5–(methylsulfonyl)benzoyl)guanidine $Na^+/H^+$ Antiporter Inhibitors".

J. B. Bream, et al, Arzneim.–Forsch. (Drug res.) 25, Nr. 10 (1975), 1477–1482, Substituted Phenylacetylguanidines: a New Class of Antihypertensive Agents.

Giulia Menozzi, et al, J. Heterocyclic Chem., 24, 1669–1675, (1987), "Reaction of 2–Dimethylaminomethylene–1,3–diones with Dinucleophiles. VI. Synthesis of ethyl or Methyl 1,5–Disubstituted 1H–Pyrazole–4–carboxylates".

* cited by examiner

*Primary Examiner*—Evelyn Mei Huang
(74) *Attorney, Agent, or Firm*—Peter C. Richardson; Gregg C. Benson; Arlene K. Musser

(57) ABSTRACT

Methods of preparing NHE-1 disclosed. The NHE-1 inhibitors are useful for the reduction of tissue damage resulting from tissue ischemia.

5 Claims, No Drawings

US 6,441,176 B1

METHOD FOR PREPARING SODIUM-HYDROGEN EXCHANGER TYPE 1 INHIBITOR

This application claims priority from provision application U.S. serial No. 60/162,377 filed Oct. 29, 1999, the benefit of which is hereby claimed under 37 C.F.R.§1.78(a)(3).

BACKGROUND OF INVENTION

This invention relates to sodium-hydrogen exchanger type 1 (NHE-1) inhibitors and methods of making such inhibitors.

Mycardial ischemic injury can occur in out-patient as well as in perioperative settings and can lead to the development of sudden death, myocardial infarction or congestive heart failure. There is an unmet medical need to prevent or minimize myocardial ischemic injury, particularly perioperative myocardial infarction. Such a therapy is anticipated to be life-saving and reduce hospitalizations, enhance quality of life and reduce overall health care costs of high risk patients.

Pharmacological cardioprotection would reduce the incidence and progression of myocardial infarction and dysfunction occurring in these surgical settings (perioperatively). In addition to reducing myocardial damage and improving post-ischemic myocardial function in patients with ischemic heart disease, cardioprotection would also decrease the incidence of cardiac morbidity and mortality due to myocardial infarction and dysfunction in patients "at risk" (such as greater than 65 years, exercise intolerant, coronary artery disease, diabetes mellitus, hypertension) that require non-cardiac surgery.

The mechanism(s) responsible for the myocardial injury observed after ischemia and reperfusion is not fully understood.

A variety of publications have disclosed the use of guanidine derivatives as useful for the treatment of, for example, arrhythmias.

A recent published patent application, PCT/IB99/00206 published as WO 99/43663 on Sep. 2, 1999, the disclosure of which is hereby incorporated by reference, discloses a variety of NHE-1 inhibitors including [5-cyclopropyl-1-(quinolin-5-yl)-1H-pyrazole4-carbonyl]guanidine.

J. Med. Chem. 1997, 40, 2017–2034 "(2-Methyl-5-(methylsulfonyl)benzoyl)guanidine Na+/H+ Antiporter Inhibitors" and Arzneim.-Forsch. (Drug Res.) 25, Nr. 10 (1975) "Substituted Phenylacetylguanidines: a New Class of Antihypertensive Agents" disclose synthesizing acyl guanidine via coupling of an ester and guanidine, in addition to an acid chloride and guanidine wherein the substrates are aromatic monocyclic structures.

Further, J. Heterocyclic Chem., 24, 1669 (1987) "Reaction of 2-Dimethylaminomethylene-1,3-diones with Dinucleophiles. VI. Synthesis of Ethyl or Methyl 1,5-Disubstituted 1H-Pyrazole4-carboxylates" discloses the preparation of esters of 5-substituted 1-phenyl-1H-pyrazole-4-carboxylic acids.

Thus, there is clearly a need and a continuing search in this field of art for compounds for the treatment of perioperative myocardial ischemia, and accordingly methods for making such compounds.

SUMMARY OF THE INVENTION

One aspect of this invention is directed to a process for preparing N-(5-cyclopropyl-1-quinolin-5-yl-1H-pyrazole4-carbonyl)-guanidine, monomesylate salt comprising combining N-(5-cyclopropyl-1-quinolin-5-yl-1H-pyrazole4-carbonyl)-guanidine with methanesulfonic acid.

Preferably the combination is performed in a polar aprotic solvent at a temperature of about 40° C. to about 80° C. It is also preferred that the solvent is a mixture of acetone and 1-methyl-2-pyrrolidinone.

Another aspect of this invention is directed to a process for preparing N-(5-cyclopropyl-1-quinolin-5-yl-1H-pyrazole-4-carbonyl)-guanidine comprising:

a. combining 5-cyclopropyl-1-quinolin-5-yl-1H-pyrazole-4-carboxylic acid and thionyl chloride in toluene to form 5-cyclopropyl-1-quinolin-5-yl-1H-pyrazole-4-carboxylic acid chloride; and b. combining guanidine hydrochloride and sodium hydroxide with a suspension of 5-cyclopropyl-1-quinolin-5-yl-1H-pyrazole4-carboxylic acid chloride in tetrahydrofuran at a temperature of about –10° C. to about 10° C. for about 1 hour to about 3 hours.

Preferably the 5-cyclopropyl-1-quinolin-5-yl-1H-pyrazole-4-carboxylic acid and thionyl chloride are combined at a temperature of about 60° C. to about 90° C. for about one to about three hours. It is also preferred that the 5-cyclopropyl-1-quinolin-5-yl-1H-pyrazole4-carboxylic acid is prepared by hydrolysis with methanol in the presence of sodium hydroxide at reflux.

Another aspect of this invention is directed to a process for preparing 5-cyclopropyl-1-quinolin-5-yl-1H-pyrazole-4-carboxylic acid methyl ester comprising: combining quinolin-5-yl-hydrazine and methyl-3-cyclopropyl-2-dimethylenamino-3-oxopropanoate in a reaction-inert solvent in the presence of an amine base.

Preferably the solvent is ethanol, the amine base is triethylamine and the combination occurs at a temperature of about 50° C. to about reflux.

Another aspect of this invention is directed to a process for preparing methyl-3-cyclopropyl-2-dimethylenamino-3-oxopropanoate comprising: combining methyl-3-cyclopropyl-3-oxopropanoate and N,N-dimethylformamide dimethylacetal at a temperature of about 50° C. to about 110° C. for about one to about five hours under neat conditions.

Another aspect of this invention is directed to a process for preparing N-(5-cyclopropyl-1-quinolin-5-yl-1H-pyrazole4-carbonyl)-guanidine, monomesylate salt comprising:

a. combining methyl-3-cyclopropyl-3-oxopropanoate and N,N-dimethylformamide dimethylacetal at a temperature of about 50° C. to about 110° C. for about one to about five hours under neat conditions;

b. combining quinolin-5-yl-hydrazine and methyl-3-cyclopropyl-2-dimethylenamino-3-oxopropanoate in a reaction-inert solvent in the presence of an amine base to form 5-cyclopropyl-1-quinolin-5-yl-1H-pyrazole4-carboxylic acid methyl ester;

c. hydrolyzing the 5-cyclopropyl-1-quinolin-5-yl-1H-pyrazole-4-carboxylic acid methyl ester with methanol in the presence of sodium hydroxide at reflux to form 5-cyclopropyl-1-quinolin-5-yl-1H-pyrazole-4-carboxylic acid;

d. combining 5-cyclopropyl-1-quinolin-5-yl-1H-pyrazole4-carboxylic acid and thionyl chloride to form 5-cyclopropyl-1-quinolin-5-yl-1H-pyrazole4-carboxylic acid chloride;

e. combining guanidine hydrochloride and sodium hydroxide with a suspension of 5-cyclopropyl-1- quinolin-5-yl-1H-pyrazole4-carboxylic acid chloride in tetrahydrofuran at a temperature of about −10° C. to about 10° C. for about 1 hour to about 3 hours to form N-(5-cyclopropyl-1-quinolin-5-yl-1H-pyrazole4-carbonyl)-guanidine; and f. combining N-(5-cyclopropyl-1-quinolin-5-yl-1H-pyrazole4-carbonyl)-guanidine with methanesulfonic acid to form N-(5-cyclopropyl-1-quinolin-5-yl-1H-pyrazole-4-carbonyl)-guanidine, monomesylate salt.

In comparison to the procedures disclosed in WO99/43663 published on Sep. 2, 1999, the instant invention provides various advantages. For example, formation of the acid chloride with thionyl chloride in toluene is preferred because the HCl salt of the acid chloride is isolated as a solid directly from the reaction. Treatment of the acid chloride in tetrahydrofuran (THF) with guanidine HCl and aqueous sodium hydroxide at lower temperatures results in increased purity and higher yields. Higher temperatures result in increased hydrolysis of the acid chloride as well as formation of other by-products.

By "pharmaceutically acceptable" it is meant the carrier, diluent, excipients, and/or salt must be compatible with the other ingredients of the formulation, and not deleterious to the recipient thereof.

As used herein, the expressions "reaction-inert solvent" and "inert solvent" refers to a solvent or mixture of solvents which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention are also included.

Other features and advantages will be apparent from the description and claims which describe the invention.

DETAILED DESCRIPTION OF THE INVENTION

In general the compound of this invention, [5-cyclopropyl-1-(quinolin-5-yl)-1H-pyrazole4-carbonyl]-guanidine and salts thereof (including the monomesylate salt), can be made by processes which include processes known in the chemical arts, particularly in light of the description contained herein. Certain processes for the manufacture of the compound of this invention are provided as further features of the invention and are illustrated by the following reaction schemes. Other processes are described in the experimental section.

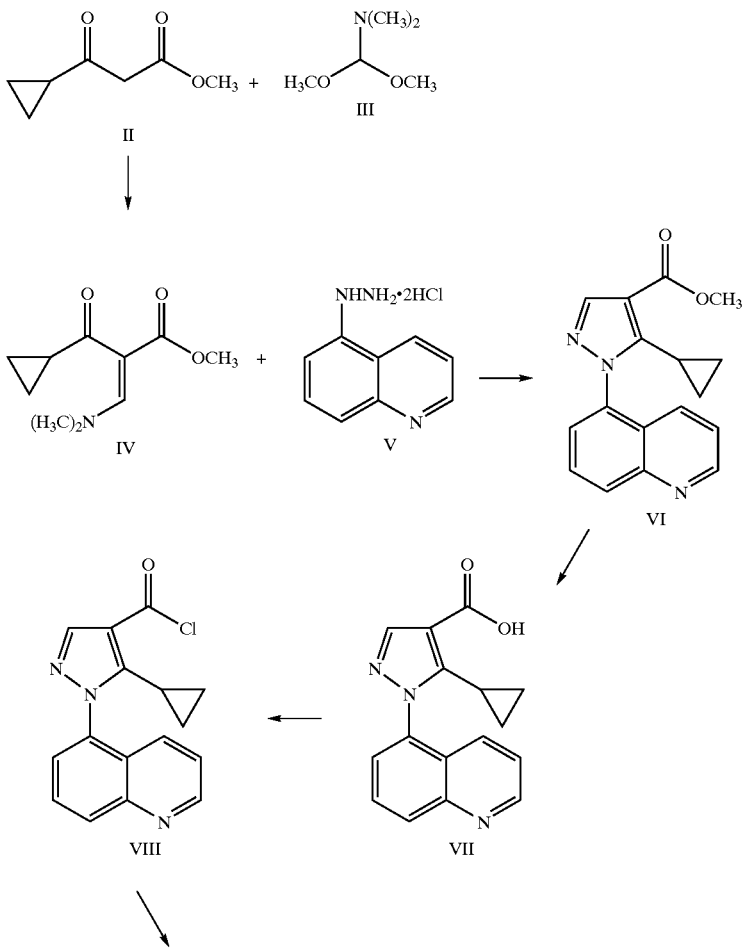

SCHEME I

-continued

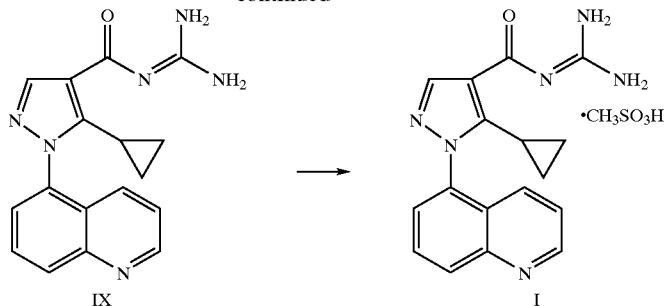

According to Scheme I the Formula II compound is combined with excess Formula III compound, N,N-dimethyl amide dimethyl acetal, optionally, in the presence of an acid catalyst such as p-toluenesulfonic acid, under neat conditions at a temperature of about 50° C. to about 110° C. for about one to about five hours, preferably at a temperature of about 70° C. to about 80° C. for about one to about two hours to prepare the Formula IV compound. This reaction can be run in ethyl acetate as well.

The Formula IV compound is cyclized with a Formula V compound in an inert solvent such as ethanol, preferably in the presence of an amine base such as triethylamine at a temperature of about 50° C. to about reflux (78° C.) for about 1 hour to about four hours to form the Formula VI pyrazole compound. This reaction may also be performed in ethyl acetate and methanol.

The Formula VI pyrazole is hydrolyzed with a base such as sodium hydroxide in a solvent such as methanol conveniently at ambient temperature or preferably at elevated temperature (e.g., reflux) for about one hour to about five hours to prepare the Formula VII acid.

Generally, the Formula VII acid is coupled with guanidine in the presence of a suitable coupling agent. A suitable coupling agent is one which transforms a carboxylic acid into a reactive species which forms an amide linkage on reaction with an amine.

The coupling agent may be a reagent which effects this condensation in a one pot process when mixed together with the carboxylic acid and guanidine. Exemplary coupling reagents are 1-(3-dimethylaminopropyl)-3-ethylcarbodiimide hydrochloride-hydroxybenzotriazole (EDC/HOBT), dicyclohexylcarbodiimide/hydroxybenzotriazole(HOBT), 2-ethoxy-1-ethoxycarbonyl-1,2-dihydroquinoline (EEDQ), and diethylphosphorylcyanide. The coupling is performed in an inert solvent, preferably an aprotic solvent at a temperature of about −20° C. to about 50° C. for about 1 to about 48 hours, in the presence of excess guanidine as base. Exemplary solvents include acetonitrile, dichloromethane, dimethylformamide and chloroform or mixtures thereof.

Preferably, the coupling agent is also that agent which converts the carboxylic acid to an activated intermediate which is isolated and/or formed in a first step and allowed to react with guanidine in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate or propanephosphonic anhydride (propanephosphonic acid anhydride, PPA) (with a tertiary amine base) to form a mixed anhydride of the carboxylic acid, or carbonyldiimidazole to form an acylimidazole. If the coupling agent is oxalyl chloride, it is advantageous to employ a small amount of dimethylformamide as cosolvent with another solvent (such as dichloromethane) to catalyze the formation of the acid chloride. This activated acid derivative may be coupled by mixing with the intermediate in an appropriate solvent together with an appropriate base. Appropriate solvent/base combinations are, for example, dichloromethane, dimethylformamide or acetonitrile or mixtures thereof in the presence of excess guanidine as base. Other appropriate solvent/base combinations include water or a ($C_1$–$C_5$)alcohol or a mixture thereof together with a cosolvent such as dichloromethane, tetrahydrofuran or dioxane and a base such as sodium, potassium or lithium hydroxide in sufficient quantity to consume the acid liberated in the reaction. Use of these coupling agents and appropriate selection of solvents and temperatures are known to those skilled in the art or can be readily determined from the literature in light of this description. These and other exemplary conditions useful for coupling carboxylic acids are described in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

In a preferred embodiment, the Formula VII acid is activated with an excess of thionyl chloride (e.g., 3 to 6 equivalents) in an aprotic solvent such as toluene at a temperature of about 60° C. to about 90° C. for about fifteen minutes to about two hours, preferably at a temperature of about 75° C. for about one to about two hours.

The resulting Formula VIII activated acid chloride in anhydrous tetrahydrofuran is combined with excess guanidine hydrochloride and an aqueous solution of an inorganic base (e.g., sodium hydroxide) in tetrahydrofuran at a temperature of about −20° C. to about 10° C. for about one hour to about three hours with warming to ambient temperature over the last hour to prepare the Formula IX compound.

The Formula IX compound is combined with methanesulfonic acid in an aprotic solvent, preferably a mixture of acetone and 1-methyl-2-pyrrolidinone, preferably about 90% to 60% acetone, the remainder 1-methyl-2-pyrrolidinone, at a temperature of about 40° C. to about 80° C. for about 10 minutes to about one hour followed by stirring at a temperature of about 20° C. to about 30° C. for about 3 hours to about 6 hours, preferably at a temperature of about ambient for about 5 hours in the absence of light. Preferably the solids are reslurried in acetone for about 6 to about 17 hours. The salt formation can also be performed in tetrahydrofuran. With this choice of solvents, a 95% ethanol reslurry is preferred.

The starting materials and reagents for the above described compounds, are also readily available or can be easily synthesized by those skilled in the art using conventional methods of organic synthesis. For example, some of the compounds used herein are related to, or are derived from compounds found in nature, in which there is a large scientific interest and commercial need, and accordingly such compounds are commercially available or are reported in the literature or are easily prepared from other commonly available substances by methods which are reported in the literature.

Those skilled in the art will recognize that many of the compounds used in the processes herein can exist in several tautomeric forms. All such tautomeric forms are considered as part of this invention. For example, all of the tautomeric forms of the carbonylguanidine moiety of the compounds are included in this invention.

The compound of this invention [5-cyclopropyl-1-(quinolin-5-yl)-1H-pyrazole-4-carbonyl]-quanidine is basic and it forms a salt with a pharmaceutically acceptable anion. All such salts, including di-salts are within the scope of this invention and they can be prepared by conventional methods. For example, they can be prepared simply by contacting the acidic and basic entities, in either an aqueous, non-aqueous or partially aqueous medium. The salts are recovered either by filtration, by precipitation with a non-solvent followed by filtration, by evaporation of the solvent, or, in the case of aqueous solutions, by lyophilization, as appropriate.

In addition, when the compound of this invention forms metabolites, hydrates or solvates they are also within the scope of the invention.

Those skilled in the art will recognize that other cardiovascular agents for example β-blockers (e.g., acebutolol, atenolol, bopindolol, labetolol, mepindolol, nadolol, oxprenol, pindolol, propranolol, sotalol), calcium channel blockers (e.g., amlodipine, nifedipine, nisoldipine, nitrendipine, verapamil), ACE inhibitors (e.g., captopril, enalapril), nitrates (e.g., isosorbide dinitrate, isosorbide 5-mononitrate, glyceryl trinitrate), diuretics (e.g., hydrochlorothiazide, indapamide, piretanide, xipamide), glycosides (e.g., digoxin, metildigoxin), thrombolytics (e.g., tPA), platelet inhibitors (e.g., reopro), aspirin, dipyridamol, potassium chloride, clonidine, prazosin, aldose reductase inhibitors (e.g., Zopolrestat) and adenosine $A_3$ receptor agonists may be used in conjunction with the compound of this invention.

The compound of the present invention inhibits the sodium/proton (Na+/H+) exchange transport system and hence is useful as a therapeutic or prophylactic agent for diseases caused by the acceleration of the sodium/proton (Na+/H+) exchange transport system, for example, cardiovascular diseases [e.g., arteriosclerosis, hypertension, arrhythmia (e.g., ischemic arrhythmia, arrhythmia due to myocardial infarction, arrhythmia after PTCA or after thrombolysis, etc.), angina pectoris, cardiac hypertrophy, myocardial infarction, heart failure (e.g., congestive heart failure, acute heart failure, cardiac hypertrophy, etc.), restenosis after PTCA, shock (e.g., hemorrhagic shock, endotoxin shock, etc.)], renal diseases (e.g. diabetes, mellitus, diabetic nephropathy, ischemic acute renal failure, etc.) organ disorders associated with ischemia or ischemic reperfusion [(e.g., heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g., ischemic stroke, hemorrhagic stroke, etc.), cerebro ischemic disorders (e.g., disorders associated with cerebral infarction, disorders caused after cerebral apoplexy as sequelae, or cerebral edema.

The compound of this invention can be used as an agent for myocardial protection in patients presenting with ongoing cardiac (acute coronary syndromes, e.g. myocardial infarction or unstable angina) or cerebral ischemic events (e.g., stroke). The compound of this invention can also be used as an agent for chronic myocardial protection in patients with diagnosed coronary heart disease (e.g., previous myocardial infarction or unstable angina) or patients who are at high risk for myocardial infarction (e.g., age greater than 65 and two or more risk factors for coronary heart disease).

The compound of this invention is effective at reducing tissue damage (e.g., substantially preventing tissue damage, inducing tissue protection) resulting from ischemia.

Preferred ischemic tissues taken individually or as a group are cardiac, brain, liver, kidney, lung, gut, skeletal muscle, spleen, pancreas, nerve, spinal cord, retina tissue, the vasculature, or intestinal tissue. An especially preferred ischemic tissue is cardiac tissue. The ischemic damage may occur during organ transplantation.

In addition to this, the compound of this invention is notable for its strong inhibitory effect on the proliferation of cells, for example the proliferation of fibroblast cells and the proliferation of the smooth muscle cells of the blood vessels. For this reason, the compound of this invention is valuable as therapeutic agent for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, glomerular nephrosclerosis, organ hypertrophies or hyperplasias, in particular hyperplasia or hypertrophy of the prostate, pulmonary fibrosis, diabetic complications or recurrent stricture after PTCA, or diseases caused by endothelial cell injury.

The utility of the compound of the present invention as a medical agent in the treatment of diseases, such as are detailed herein in mammals (e.g., humans) for example, myocardial protection during surgery or mycardial protection in patients presenting with ongoing cardiac or cerebral ischemic events or chronic cardioprotection in patients with diagnosed coronary heart disease, is demonstrated by the activity of the compound of this invention in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)]. Such assays also provide a means whereby the activity of the compound of this invention can be compared with the activities of other known compounds. The results of these comparisons are useful for determining dosage levels in mammals, including humans, for the treatment of such diseases.

Administration of the compound of this invention can be via any method which delivers a compound of this invention preferentially to the desired tissue (e.g., liver and/or cardiac tissues). These methods include oral routes, parenteral, intraduodenal routes, etc. Generally, the compound of the present invention may be administered in single (e.g., once daily) or multiple doses or via constant infusion.

The compound of this invention is useful, for example, in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). The active compound is therefore usefully employed prophylactically to prevent, i.e. (prospectively or prophylactically) to blunt or stem, tissue damage (e.g., myocardial tissue) in patients who are at risk for ischemia (e.g., myocardial ischemia).

Generally, the compound of this invention may be administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

The amount and timing of compound administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

Thus, for example, in one mode of administration the compound of this invention may be administered just prior to cardiac surgery (e.g., within twenty-four hours before surgery) and/or during and/or subsequent to cardiac surgery (e.g., within twenty-four hours after surgery) where there is risk of myocardial ischemia. In an especially preferred mode an infusion is administered with a loading dose of about 1 mg to about 300 mg for about one minute to about one hour prior to surgery followed by a constant infusion of about 1 mg/kg/day to about 100 mg/kg/day for the remaining presurgery, surgery and postsurgery periods, including for example about 2 to about 7 days post surgical treatment. The compounds of this invention may also be administered in a chronic daily mode.

An amount of the compound of this invention is used that is effective for ischemic protection. A preferred dosage is about 0.001 to about 100 mg/kg/day of the compound of this invention. An especially preferred dosage is about 0.01 to about 50 mg/kg/day of the compound of this invention.

The compound of the present invention is generally administered in the form of a pharmaceutical composition comprising the compound of this invention together with a pharmaceutically acceptable carrier, vehicle or diluent. Thus, the compound of this invention can be administered individually or together with another agent in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various preservatives, buffers, sweetening agents, flavoring agents, coloring agents, emulsifying agents and/or suspending agents, as well as such diluents as water, ethanol, propylene glycol, glycerin and various like combinations thereof.

For purposes of parenteral administration, solutions, for example, in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose, etc. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to about 5% concentration), nonaqueous solutions, otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain, for example, 0.0001%–95% of the compound(s) of this invention. In any event, the composition or formulation to be administered will contain a quantity of the compound according to the invention in an amount effective to treat the disease/condition of the subject being treated.

The compound of this invention generally will be administered in a convenient formulation. The following formulation example is illustrative only and is not intended to limit the scope of the present invention.

In the formulation which follows, "active ingredient" means a compound of this invention.

An intravenous formulation is prepared as follows:

| Formulation 1: Intravenous Solution | |
| --- | --- |
| Ingredient | Quantity |
| Active ingredient | 25 mg |
| Isotonic saline | 1,000 mL |

The solution of the above ingredients is intravenously administered to a patient.

The active ingredient above may also be a combination of agents.

EXAMPLES

Example 1

Methyl-3-cyclopropyl-3-oxopropanoate (15 g, 106 mmol, 1 equiv) and N,N-dimethylformamide dimethylacetal (14.7 mL, 111 mmol, 1.05 equiv) were heated at 75° C. for 1.5 h under N$_2$. The resulting orange oil was then cooled to room temperature. TLC analysis (1:1 EtOAc/hexanes) indicates disappearance of starting material and appearance of a minor less polar spot and a major more polar spot (methyl-3-cyclopropyl-2-dimethylenamino-3-oxopropanoate). The crude mixture was used as is in the next step.

Example 2

Crude methyl-3-cyclopropyl-2-dimethylenamino-3-oxopropanoate (20.9 g, 106 mmol, 1.07 equiv) was diluted with ethanol (250 mL). Triethylamine (34.4 mL, 247 mmol, 2.5 equiv) followed by quinolin-5-yl-hydrazine (22.9 g, 98.6 mmol, 1 equiv) was added sequentially. Slight gas evolution upon addition of quinolin-5-yl-hydrazine was observed. The resulting heterogeneous mixture was heated at reflux (78° C.) under N$_2$ for 2 h. The mixture became homogeneous and very dark after about 3 min of heating. The mixture was then cooled to room temperature. TLC analysis (1:1 EtOAc/hexanes) indicates a slightly less polar spot (5-cyclopropyl-1-quinolin-5-yl-1H-pyrazole4- carboxylic acid methyl ester). APCI mass spec indicates desired product as well. The reaction mixture was then concentrated. To the residue was added EtOAc (300 mL) and 0.1N HCl (400 mL). This emulsion was stirred for 10 min at room temperature and then filtered through a pad of Celite® to remove solids. The resulting biphasic mixture was separated. The aqueous layer was extracted with EtOAc (2×300 mL). The combined organic layers were washed with 0.1N HCl (2×300 mL), then dried over sodium sulfate, and concentrated. To the residue was added hot isopropyl ether (80 mL). The resulting cloudy solution was stirred for 2 min. Then hexanes (125 mL) were added. The solids were allowed to granulate overnight. Solids were collected by filtration to provide the product 5-cyclopropyl-1-quinolin-5-yl-1H-pyrazole4-carboxylic acid methyl ester as a yellow orange powder (20.8 g, 72% over 2 steps).

Example 3

To a solution of 5-cyclopropyl-1-quinolin-5-yl-1H-pyrazole4-carboxylic acid methyl ester (20 g, 68.2 mmol, 1 equiv) in MeOH (120 mL) was added 2N NaOH (54.5 mL, 109 mmol, 1.6 equiv). The resulting solution was heated at reflux (65° C.) for 1.5 h under N$_2$, and then allowed to cool to room temperature. TLC analysis (1:1 EtOAc/hexanes) indicates disappearance of starting material. The methanol was removed under vacuum with gentle heating (35° C.) on a rotovap. The basic aqueous layer was then washed with EtOAc (2×100 mL). The resulting basic aqueous layer was acidified slowly to pH 1 to 2 with concentrated HCl. The product precipitated out during acidification. The slurry was stirred at room temperature for 0.5 h, then the solids were collected by filtration. The solids were washed with 1N HCl (2×25 mL) and dried to afford the acid as a pale brown solid (18.8 g, 99%).

Example 4

To a stirred suspension of 5-cyclopropyl-1-quinolin-5-yl-1H-pyrazole4-carboxylic acid (25 g, 89.5 mmol, 1 equiv) in toluene (250 mL) was added thionyl chloride (32.6 mL, 448 mmol, 5 equiv). The resulting suspension was heated at 75° C. for 1.5 h under N$_2$. The reaction mixture stayed heterogeneous throughout. The solid acid chloride was collected by filtration. The tan solid was washed with toluene (3×50 mL) and dried under vacuum. A suspension of the acid chloride in THF (250 mL) was cooled to 0° C. An aqueous solution of guanidine hydrochloride (17.1g, 179 mmol, 2 equiv) and 2N NaOH (224 mL, 448 mmol, 5 equiv) was added via a dropping addition funnel over 5–10 min under N$_2$. The reaction became homogenous and biphasic upon addition of the basic aqueous solution of guanidine. The mixture was stirred at 0° C. with slow warming over 1 h to room temperature and then for an additional 1 h at room temperature. TLC analysis (4:1 dichloromethane/methanol) indicates appearance of a more polar spot (N-(5-Cyclopropyl-1-quinolin-5-yl-1H-pyrazole-4-carbonyl)-guanidine) and trace starting material acid. THF was removed under vacuum with gentle heating (35° C.) which resulted in precipitation of the product. The aqueous layer was stirred at room temperature for 1 h to allow the product to granulate. The solid was collected by filtration, washed with water (2×50 mL), and dried. The color of the product ranged from off-white to medium brown. This batch was medium brown. Reslurry in MeOH (125 mL) for 30 min provided the desired product, N-(5-cyclopropyl-1-quinolin-5-yl-1H-pyrazole-4-carbonyl)-guanidine (22.6 g, 79% yield) as a pale tan solid.

Example 5

N-(5-cyclopropyl-1-quinolin-5-yl-1H-pyrazole4-carbonyl)-guanidine (3.08 kg, 9.61 mol, 1 equiv) was suspended in acetone (30.8 kg). 1-Methyl-2-pyrrolidinone (12.3 kg) was added to obtain a homogenenous solution. An additional 4.8 kg of acetone was used to rinse forward (spec. free filtration). The reaction solution was warmed to 50° C. A solution of methanesulfonic acid (0.83 kg, 8.65 mol, 0.9 equiv) in acetone (8.3 kg) was added while keeping the temperature below 55° C. The slurry that was obtained was agitated at 50° C. for 1 to 2 hours, then cooled, and filtered. The filter cake was rinsed with acetone and then dried to afford N-(5-cyclopropyl-1 -quinolin-5-yl-1H-pyrazole4-carbonyl)-guanidine, monomesylate salt (3.24 kg, 81%) as an off-white solid.

Example 6

To 3.165 kg of the product of Example 5 was added 123 Liters (3.8 volumes) of acetone. The slurry was agitated for 20 hours at room temperature. The slurry was filtered, and the solids were dried at 50° C.The product was an anhydrous crystal (3.145 kg, 99%) having equant form—M.P. (onset) 228° C.

What is claimed is:

1. A process for making N-(5-cyclopropyl-1-quinolin-5-yl-1H-pyrazole-4-carbonyl)-guanidine comprising:
   a. combining quinolin-5-yl-hydrazine and methyl-3-cyclopropyl-2-dimethylenamino-3-oxopropanoate in a reaction-inert solvent in the presence of an amine base to form 5-cyclopropyl-1-quinolin-5-yl-1H-pyrazole-4-carboxylic acid methyl ester;
   b. hydrolyzing the 5-cyclopropyl-1-quinolin-5-yl-1H-pyrazole-4-carboxylic acid methyl ester to form 5-cyclopropyl-1-quinolin-5-yl-1H-pyrazole-4-carboxylic acid;
   c. combining the 5-cyclopropyl-1-quinolin-5-yl-1H-pyrazole-4-carboxylic acid and thionyl chloride in toluene to form 5-cyclopropyl-1-quinolin-5-yl-1H-pyrazole-4-carboxylic acid chloride; and
   d. combining guanidine hydrochloride and sodium hydroxide to a suspension of the 5-cyclopropyl-1-quinolin-5-yl-1H-pyrazole-4-carboxylic acid chloride in tetrahydrofuran at a temperature of about −10° C. to about 10° C. for about 1 hour to about 3 hours.

2. A process as recited in claim 1 wherein 5-cyclopropyl-1-quinolin-5-yl-1H-pyrazole-4-carboxylic acid and thionyl chloride are combined at a temperature of about 60° C. to about 90° C. for about one to about three hours.

3. A process as recited in claim 1 wherein the 5-cyclopropyl-1-quinolin-5-yl-1H-pyrazole-4-carboxylic acid is prepared by hydrolysis with methanol in the presence of sodium hydroxide at reflux.

4. A process as recited in claim 1 wherein in step a, the reaction-inert solvent is ethanol, the amine base is triethylamine and the combination occurs at a temperature of about 50° C. to about reflux.

5. A process for making N-(5-cyclopropyl-1-quinolin-5-yl-1H-pyrazole-4-carbonyl)-guanidine, monomesylate salt comprising:

a. combining methyl-3-cyclopropyl-3-oxopropanoate and N,N-dimethylformamide dimethylacetal at a temperature of about 50° C. to about 110° C. for about one to about five hours under neat conditions;

b. combining quinolin-5-yl-hydrazine and methyl-3-cyclopropyl-2-dimethylenamino-3-oxopropanoate in a reaction-inert solvent in the presence of an amine base to form 5-cyclopropyl-1-quinolin-5-yl-1H-pyrazole4-carboxylic acid methyl ester;

c. hydrolyzing the 5-cyclopropyl-1-quinolin-5-yl-1H-pyrazole-4-carboxylic acid methyl ester in methanol in the presence of sodium hydroxide at reflux to form 5-cyclopropyl-1-quinolin-5-yl-1H-pyrazole-4-carboxylic acid;

d. combining 5-cyclopropyl-1-quinolin-5-yl-1H-pyrazole-4-carboxylic acid and thionyl chloride to form 5-cyclopropyl-1-quinolin-5-yl-1H-pyrazole-4-carboxylic acid chloride;

e. combining guanidine hydrochloride and sodium hydroxide to a suspension of 5-cyclopropyl-1-quinolin-5-yl-1H-pyrazole-4-carboxylic acid chloride in tetrahydrofuran at a temperature of about −10° C. to about 10° C. for about 1 hour to about 3 hours to form N-(5-cyclopropyl-1-quinolin-5-yl-1H-pyrazole-4-carbonyl)-guanidine; and f. combining N-(5-cyclopropyl-1-quinolin-5-yl-1H-pyrazole-4-carbonyl)-guanidine with methanesulfonic acid to form N-(5-cyclopropyl-1-quinolin-5-yl-1H-pyrazole-4-carbonyl)-guanidine, monomesylate salt.

\* \* \* \* \*